United States Patent
Okada et al.

(10) Patent No.: US 7,144,864 B2
(45) Date of Patent: Dec. 5, 2006

(54) CARBOXYPEPTIDASE R INHIBITING PEPTIDE

(75) Inventors: Hidechika Okada, Mizuho-ku (JP); Eliada Lazoura, Mizuho-ku (JP); William Campbell, Yoyohashi (JP); Noriko Okada, Mizuho-ku (JP)

(73) Assignee: Hidechika Okada (JP)

( * ) Notice: Subject to any disclaimer, the term of this patent is extended or adjusted under 35 U.S.C. 154(b) by 345 days.

(21) Appl. No.: 10/254,610

(22) Filed: Sep. 25, 2002

(65) Prior Publication Data
US 2005/0130898 A1   Jun. 16, 2005

(51) Int. Cl.
*A61K 38/08* (2006.01)
*A61K 38/00* (2006.01)
*A61K 38/02* (2006.01)
*C07K 2/00* (2006.01)
*C07K 7/04* (2006.01)

(52) U.S. Cl. ............................ 514/15; 514/2; 530/300; 530/328

(58) Field of Classification Search ...................... None
See application file for complete search history.

(56) References Cited

U.S. PATENT DOCUMENTS 5,833,986 A * 11/1998 LaRochelle et al. ..... 424/143.1
6,020,166 A * 2/2000 De Lange et al. ......... 435/69.1
6,051,549 A * 4/2000 Roberts et al. ................ 514/2

OTHER PUBLICATIONS

E. Lazoura, et al. Chem. Biol. (2002) 9(10), pp. 1129-1139.*
G.M. Hass, et al. Biochemistry (1975) 14(6), pp. 1134-1342.*
.R. Leary, et al. Biochemistry (1979) 18(11), pp. 2252-2256.*
C. Marino-Buslje, et al. Eur. J. Biochem. (2000) 267, pp. 1502-1509.*
M. Nagashima, et al. Thromb. Res. (2000) 98, pp. 333-342.*
G.M. Clore, et al. Biochemistry (1987) 26, pp. 8012-8023.*

* cited by examiner

*Primary Examiner*—Cecilia J. Tsang
*Assistant Examiner*—Andrew D. Kosar
(74) *Attorney, Agent, or Firm*—Burns & Levinson LLP; Stephen J. Gaudet; Jerry Cohen

(57) ABSTRACT

A novel carboxypeptidase R (CPR) inhibiting peptide is prepared using rational structure-based strategies, incorporating two principle facts: (a) CPR has a strong affinity for basic amino acids and; and (b) the two lysines and arginine residues of PCI are orientated in the same direction and held in close spatial proximity by three disulfide bonds.

4 Claims, 9 Drawing Sheets

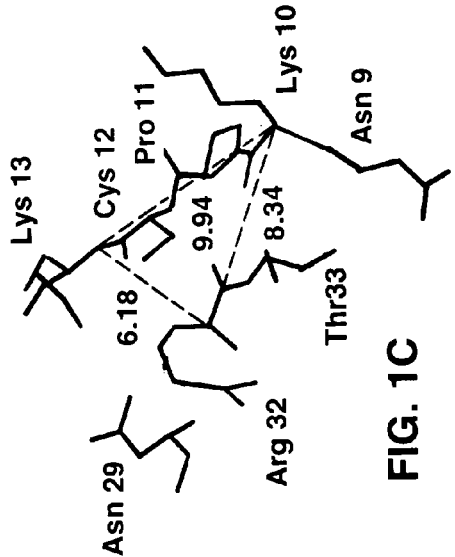
FIG. 1A
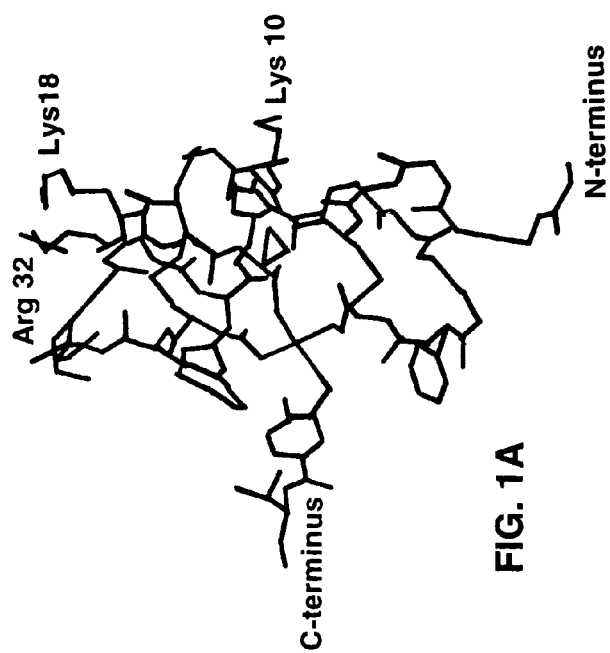
FIG. 1B
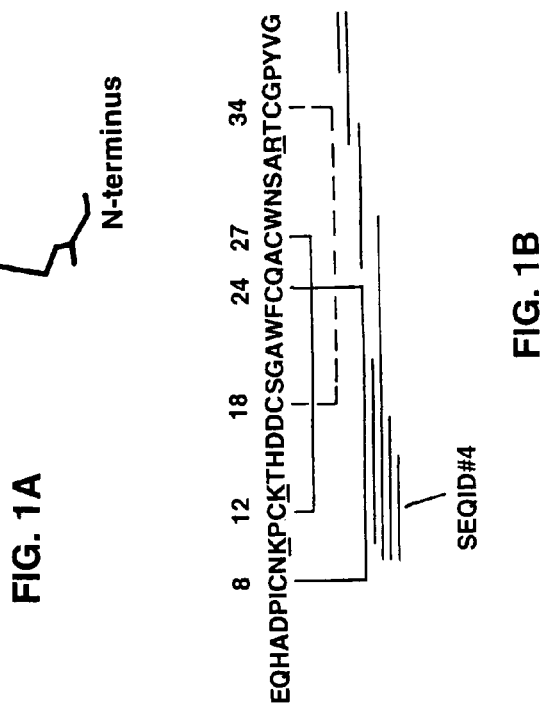
FIG. 1C
| Peptide | Sequence | Molecular Weight |
|---|---|---|
| PCI-2K(SEQID#1) | NKPCKTHDD | 1056 |
| PCI-R(SEQID#2) | QACWNSART | 1036 |
| CPI-2K-R(SEQID#1&2) | NKPCKTHDD QACWNSARRT | 2090 |
| CPI-2KR(SEQID#3) | CKPAKNARC | 989 |
| CPI-2KR-cyclic(SEQID#3) | CKPAKNARC | 987 |
FIG. 1D

| Inhibitor (I) | [I] (nM) | $K_m$ (mM) | $V_{max}$ (mM-sec$^{-1}$) | $K_{cal}$ (sec$^{-1}$) | $K_i$ (nM) | $R^2$ |
|---|---|---|---|---|---|---|
| None | 0 | 1.27 | 0.0034 | 0.0027 | N/A | 0.992 |
| PCI | 12 | 12.3 | 0.0012 | 0.0001 | 1.4 | 0.964 |
| PCI-2K-R | 239 | 4.2 | 0.0021 | 0.0008 | 407.1 | 0.998 |

FIG. 2B

EQHADPICNK (SEQID#5)
QHADPICNKP (SEQID#6)
HADPICNKPC (SEQID#7)
ADPICNKPCK (SEQID#8)
DPICNKPCKT (SEQID#9)
PICNKPCKTH (SEQID#10)
ICNKPCKTHD (SEQID#11)
CNKPCKTHDD (SEQID#12)
NKPCKTHDDC (SEQID#13)
KPCKTHDDCS (SEQID#14)
PCKTHDDSCG (SEQID#15)
CRTHDDCSGA (SEQID#16)
KTHDDCSGAW (SEQID#17)
THDDCSGAWF (SEQID#18)
HDDCSGAWFC (SEQID#19)
DDCSGAWFCQ (SEQID#20)
DCSGAWFCQA (SEQID#21)
CSGAWFCQAC (SEQID#22)
SGAWFCQACW (SEQID#23)
GAWFCQACWN (SEQID#24)
AWFCQACWNS (SEQID#25)
WFCQACWNSA (SEQID#26)
FCQACWNSAR (SEQID#27)
CQACWNSART (SEQID#28)
QACWNSARTC (SEQID#29)
ACWNSARTCG (SEQID#30)
CWNSARTCGP (SEQID#31)
WNSARTCGPY (SEQID#32)
NSARTCGPYV (SEQID#33)
SARTCGPYVG (SEQID#34)

FIG. 2C

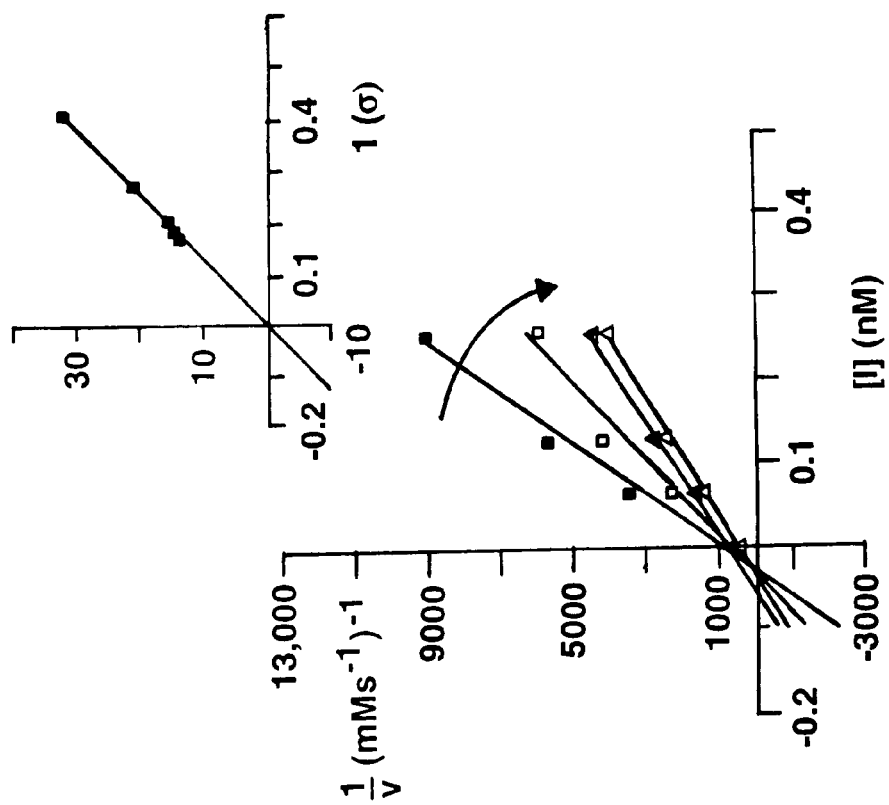
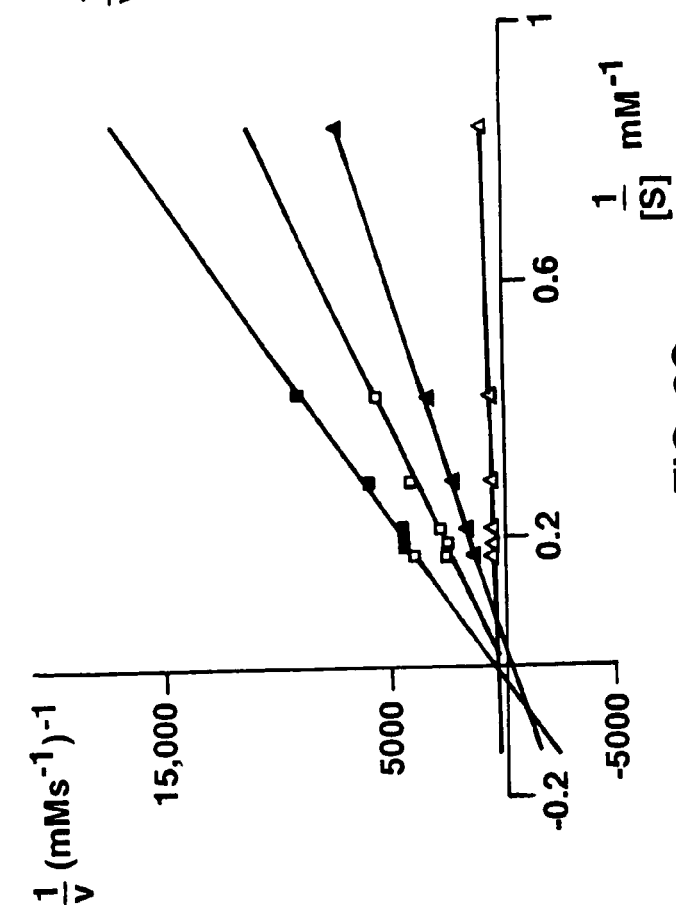
FIG. 3C
FIG. 3D

| Inhibitor (I) | [I] (nM) | $K_m$ (Mm) | $V_{max}$ (Mm-sec$^{-1}$) | $K_{cal}$ (sec$^{-1}$) | $K_I$ (nM) | $R^2$ |
|---|---|---|---|---|---|---|
| None | 0 | 1.4 | 0.0025 | 0.001081 | N/A | 0.991 |
| CPI-2KR | 253 | 41.7 | 0.0021 | 0.000049 | 8.8 | 0.991 |

FIG. 3E

|  | α-Helix | β-Sheet | β-Turn | Random |
|---|---|---|---|---|
| CPR | 35.9 | 38.1 | 11.0 | 15.0 |
| CPI-2KR | 0.0 | 16.2 | 19.6 | 64.2 |
| Complex0 | 3.0 | 48.3 | 8.6 | 40.1 |
| Complex30 | 4.9 | 50.8 | 7.9 | 36.4 |
| Arithmetic Sum | 0.0 | 47.2 | 5.1 | 47.7 |

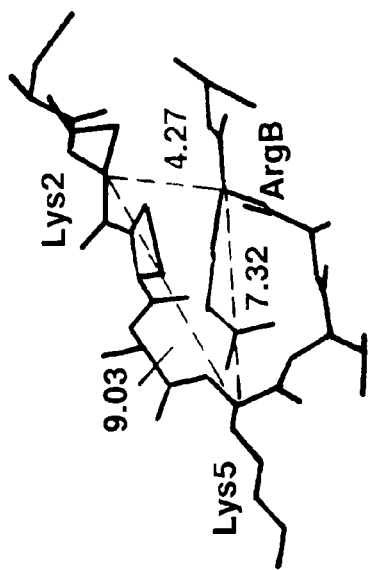
| Peptide | Lys2-Lys5 | C-C distance (Å) Lsy5-Arg8 | Arg8-Lys2 |
|---|---|---|---|
| PCI-2K-R | 6.23 | 10.55 | 9.74 |
| CPI-2KR | 9.03 | 7.32 | 4027 |
| CPI-2Kr-cyclic | 7.19 (8.02)[a] | 10.20 (6.89)[a] | 6020 (8.19)[a] |
| PCI | 9.94[b] | 6.18[b] | 8.34[b] |
FIG. 5A
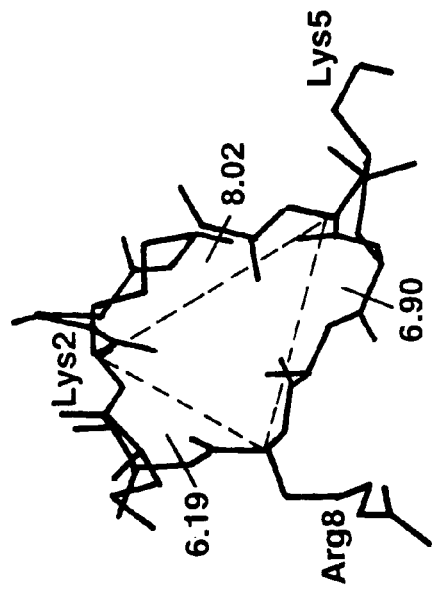
FIG. 5B
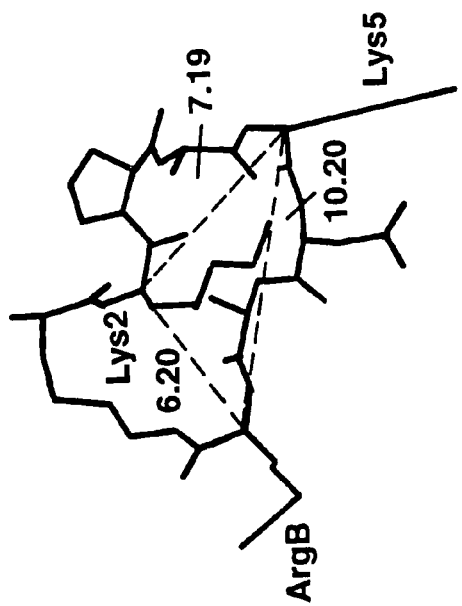
FIG. 5C
FIG. 5D

| Inhibitor | (I) (nM) | $K_m$ (mM) | $V_{max}$ (mM-sec$^{-1}$) | $K_{cal}$ (sec$^{-1}$) | R2 |
|---|---|---|---|---|---|
| None | 0 | 3.47 | 0.0013 | 0.00039 | 0.990 |
| GEMSA | 425 | 14.1 | 0.0019 | 0.00014 | 0.994 |
| GEMSA | 2126 | N/A* | N/A* | 0.00003 | 0.985 |
| CPI-2KR | 506 | 5.18 | 0.0015 | 0.00030 | 0.997 |

# CARBOXYPEPTIDASE R INHIBITING PEPTIDE

BACKGROUND OF THE INVENTION

1. Field of the Invention

This invention generally relates to a carboxypeptidase R inhibitor. More particularly, this invention relates to a peptide which inhibits activity of carboxypeptidase R so as to be effectively used in treatment of cerebral infarction, myocardial infarction and disseminated intravascular coagulation (DIC)

2. Background Art

Carboxypeptidases (CPs) are enzymes which catalyze the hydrolysis of peptide bonds at the C-terminus of peptides and proteins. They have been categorized according to their actions, either as metallocarboxypeptidases (MPs) or cysteine/serine-carboxypeptidases (Cys/Ser-CP). MPs are distinct from Cys/Ser-CPs. MPs possess a tightly bound $Zn^{2+}$ atom, which is directly involved in catalysis, while Cys/Ser-CPs contain a reactive Cys/Ser residue at their active site as the Ser/His/Asp triad of serine proteases. MPs can be further subdivided into carboxypeptidase A-like enzymes having a preference for hydrophobic C-terminal residues, and carboxypeptidase B-like enzymes having a preference for C-terminal basic residues (lysine and arginine). For review see Vendrell et al. [1].

Carboxypeptidase R (CPR) [2], also known as plasma carboxypeptidase B (CPB) [3], carboxypeptidase U (CPU) [4] or activated thrombin-activatable fibrinolysis inhibitor (TAFIa) [5], is a carboxypeptidase B-like enzyme present as a zymogen (proCPR) in plasma. CPR plays a crucial role in regulating fibrinolysis [3, 6] and acts as an inactivator of inflammatory mediators, preferentially removing C-terminal arginine (R) residues from anaphylatoxins, thereby preventing excess inflammation [7]. Carboxypeptidase N (CPN; 270 kDa glycoprotein) [8] which is also present in plasma is also an important inactivator of anaphylatoxins, kinins and fibrinopeptides [9–11]. However, in contrast to CPR, it does not play any significant role in dampening fibrinolysis. Moreover, CPN is present in an active form in plasma whereas CPR is found in the inactive proCPR state and is called into play during coagulation [2]. Previously, the carboxypeptidase activity in plasma which is responsible for inactivation of bradykinin, anaphylatoxins and other basic carboxy-terminal peptides was considered due to CPN alone [9–11]. However, CPR was also shown to inactivate bradykinin [12, 13] and furthermore, CPR, not CPN, was found to effectively reduce fibrinolysis [14].

Following its activation, CPR catalyses the removal of C-terminal lysine (K) residues from cell-surface proteins and partially degraded fibrin clots thereby preventing the binding [15, 16] and activation of plasminogen [5, 14]. Conversion of plasminogen (Glu-plasminogen) to its active form, plasmin (Lys-plasmin or Lys-plasminogen), requires tissue-plasminogen activator (t-PA) which is an activator of blood clot lysis. Binding of t-PA to fibrin via its K-binding domain catalyses cleavage of Glu-plasminogen (i.e. plasminogen) at the C-terminus of Lys76 to yield Lys-plasminogen (i.e. plasmin). Lys-plasminogen has an increased affinity for fibrin compared with Glu-plasminogen since the release of residues 1–76 exposes the kringle 1 domain, which contains two residues (Arg32 and Arg34), which were considered to be responsible for fibrin binding [17]. Studies have shown that CPR inhibits t-PA-induced lysis only when Glu-plasminogen, not Lys-plasminogen, is present, suggesting that its antifibrinolytic effect is primarily mediated through inhibition of Glu-plasminogen activation [5]. Therefore, removal of K-residues by CPR from partially degraded fibrin diminishes the already low binding affinity of Glu-plasminogen to fibrin, essentially prolonging fibrinolysis [3]. Plasmin-mediated proteolysis of fibrin constitutes a positive-feedback process that enhances plasminogen activation. CPR inhibits fibrinolysis by removing C-terminal lysine residues from fibrin, thereby limiting plasmin formation [5, 13, 14].

At present, t-PA is the only treatment for thromboembolic stroke approved by the Food and Drug Administration. However, recently adverse side effects have been reported in some patients, suggesting that t-PA may modulate N-methyl-D-aspartate (NMDA)-receptor-mediated signaling and excitotoxic neuronal death [18]. To alleviate this problem, the co-administration of potato carboxypeptidase inhibitor (PCI) with lower doses of t-PA has been suggested and recent experiments in animal models have shown that PCI dramatically enhances clot lysis [19]. PCI [20] is a small 39-residue protein (MW 4295 Da) which has the ability to selectively inhibit CPR without affecting the activity of CPN in the circulation [14]. An understanding of the interaction between CPR and PCI is crucial for the development of novel therapeutics for use in thrombolytic therapy. The inventors' studies have lead to the design of a smaller peptide inhibitor of CPR, designated as CPI-2KR, which shows similar biological activity to PCI in vitro and is a competitive inhibitor of CPR. While this peptide may be useful for the treatment and/or prevention of thrombosis, it also represents a starting point for the design of low molecular weight organic molecules, which are preferable and more useful alternatives. In this description, the rational structure-based strategies employed to design the novel CPR inhibitor are also discussed.

SUMMARY OF THE INVENTION

A novel carboxypeptidase R (CPR) inhibitor, related to potato carboxypeptidase inhibitor (PCI), was designed using rational structure-based strategies, incorporating two principle facts: (a) CPR has a strong affinity for basic amino acids and; and (b) the two lysines and arginine residues of PCI are orientated in the same direction and held in close spatial proximity by three disulfide bonds. Initially, a disulfide-bonded fragment of PCI was synthesized showing weak competitive inhibitory activity against CPR. Subsequently, a smaller linear 9-mer peptide, designated as CPI-2KR, was designed/synthesized and found to be a more efficient competitive inhibitor of CPR, without affecting the activity of the other plasma carboxypeptidase, CPN. In vitro studies showed that, together with tissue plasminogen activator, CPI-2KR synergistically accelerated fibrinolysis, indicating that it may be a useful agent for the treatment and/or prevention of thrombosis, representing a lead compound for the design of smaller organic molecules for use as an adjunct to thrombolytic therapy.

Administration of the therapeutic agents in accordance with the present invention may be continuous or intermittent, depending, e.g., upon the recipient's physiological condition, whether the purpose of the administration is therapeutic or prophylactic, and other factors known to skilled practitioners. The administration of the peptides of the present invention may be essentially continuous over a preselected period of time or may be in a series of intermittent doses.

The peptide compounds may be formulated into compositions in neutral or salt forms. Pharmaceutically acceptable nontoxic salts include the acid additive salts (formed with free amino groups) which are formed by reaction with inorganic acids such as hydrochloric, sulfuric and phosphoric acids, or organic acids such as acetic, oxalic, tartaric, mandelic, citric and malic acids. Salts formed with free carboxyl groups may be derived from inorganic bases such as sodium, potassium, ammonium, calcium, or ferric hydroxides, and such organic bases such as amines, i.e., isopropylamine, trimethylamine, 2-ethylamino ethanol, histidine and procaine.

One or more suitable unit dosage forms comprising the peptide of the invention, which may optionally be formulated for sustained release, can be administered by a variety of routes including oral or parenteral, including rectal, buccal, vaginal and sublingual, transdermal, subcutaneous, intravenous, intramuscular, intraperitoneal, intrathoracic, intracoronary, intrapulmonary and intranasal routes. The formulations may be conveniently presented in discrete unit dosage forms and may be prepared by any of the methods well known to pharmacy. Such methods may include the steps of bringing into association the therapeutic agent with liquid carriers, solid matrices, semi-solid carriers, finely divided solid carriers or combinations thereof, and, if necessary, introducing or shaping the product into the desired delivery system.

When the peptide of the present invention is prepared for oral administration, it is preferably combined with a pharmaceutically acceptable carrier, diluent or excipient to form a pharmaceutical formulation, or unit dosage form. The total active ingredients in such formulations comprise from 0.1 to 99.9% by weight of the formulation. By use of "pharmaceutically acceptable", it is meant that the carrier, diluent, excipient and/or salt must be compatible with the other ingredients of the formulation, and not deleterious to the recipient thereof. The active ingredient for oral administration may be present as a powder form or granules; a solution, suspension or emulsion; or in achievable base such as a synthetic resin for ingestion of active ingredients from a chewing gum. The active ingredient may also be presented as a bolus, electuary or paste.

Pharmaceutical formulations containing the peptide of the present invention can be prepared through procedures known in the art using well known and readily available ingredients. For example, the peptide of the invention can be formulated with common excipients, diluents or carriers, and formed into tablets, capsules, suspensions, powders and the like. Examples of such excipients, diluents and carriers that are suitable for such formulations include the fillers and extenders such as starch, sugars, mannitol and silicic derivatives; binding agents such as carboxymethyl cellulose, HPMC and other cellulose derivatives, alginates, gelatin, and polyvinyl-pyrrolodone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol and glycerol monostearate; adsorptive carriers such as kaolin and bentonite; and lubricants such as talc, calcium stearate, magnesium stearate and solid polyethyl glycols.

Tablets or caplets containing the peptide of the present invention may include buffering agents such as calcium carbonate, magnesium oxide and magnesium carbonate. Caplets and tablets may also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate and zinc stearate. Hard or soft gelatin capsules containing the peptide of the present invention may contain inactive ingredients such as gelatin, microcrystalline cellulose, sodium lauryl sulfate, starch, talc and titanium dioxide, as well as liquid vehicles such as polyethylene glycols (PEGs) and vegetable oil. Moreover, enteric coated caplets or tablets of the peptide of the invention are designed to resist disintegration in the stomach and dissolve in the more neutral to alkaline environment of the doudenum.

The peptide of the invention may also be formulated as elixirs or solutions for convenient oral administration or as solutions appropriate for parenteral administration, e.g., by intramuscular, subcutaneous or intravenous routes. The pharmaceutical formulations of the peptide of the present invention may also take a form of an aqueous or anhydrous solution or dispersion, or alternatively a form of an emulsion or suspension.

Thus, the peptide of the present invention may be formulated for parenteral administration (e.g., by injection such as bolus injection or continuous infusion) and may be presented in ampules, pre-filled syringes, small volume infusion containers or multi-dose containers with an added preservative. The active ingredients may take such forms as suspensions, solutions, or emulsions in oily or aqueous vehicles, and may contain formulary agents such as suspending, stabilizing and/or dispersing agents. Alternatively, the active ingredients may be in a powder form, obtained by aseptic isolation of sterile solid or by lyophilization from solution, for constitution with a suitable vehicle, e.g., sterile, pyrogen-free water, before use.

The mechanisms involved in the regulation of coagulation and fibrinolysis (clot lysis) are complex and include numerous protein-protein interactions. What is interesting is the discovery of proCPR (58 kDa glycoprotein), a metallocarboxypeptidase found in the plasma exhibiting carboxypeptidase B-like activity following activation. Proteolytic cleavage at Arg92 yields a 92-amino acid activation peptide (~15 kDa) and a 309-amino acid enzyme (CPR; 35 kDa). The inactive proCPR form is present in the plasma at concentrations between 70 and 275 nM, 50-fold lower than the Km value for activation [21]. Although proCPR can be activated by thrombin, the process is inefficient (Km 0.5–2.1 mM; $k_{cat}$ 0.0021 $s^{-1}$) requiring large amounts of thrombin compared with activation by plasmin (Km 55 nM; $k_{cat}$ 0.00044 $s^{-1}$) [22]. In contrast, the complex formed between thrombin and the endothelial cell receptor, thrombomodulin (TM), can more efficiently activate this zymogen (Km 0.4–1.2 $s^{-1}$) [22, 23]. Since proCPR is activated by thrombin, enzymes that regulate the formation of thrombin, such as protein C, are also most likely involved. Furthermore, the activation of both protein C and proCPR is enhanced when thrombin is bound to TM [22, 24]. Recent studies showed that although higher TM concentrations (10 and 25 nM) upregulated fibrinolysis, attributed to the activation of protein C, lower TM concentrations (<5 nM) resulted in downregulation of fibrinolysis due to proCPR activation [25].

Recently, proCPR was shown to be an acute phase protein, with upregulation of its mRNA in response to inflammation [26, 27]. On the other hand, in diseases where circulating TM levels are elevated such as diabetes mellitus with microangiopathy, disseminated intravascular coagulation (DIC) and systemic lupus erythromatosus, the upregulation may result in enhanced susceptibility to thrombosis. It has been shown that proCPR levels exceeding 129 nM correlate with a 2-fold increase in risk for deep vein thrombosis [28]. Therefore, the development of a CPR inhibitor for use in thrombolytic therapy is highly desirable.

BRIEF DESCRIPTION OF THE DRAWINGS

FIG. 1 shows a potato carboxypeptidase inhibitor (PCI), wherein FIG. 1A shows a crystal structure of PCI from 4CPA showing the primary and secondary binding sites of PCI to CPA, where the two lysine and single arginine residues responsible for inhibiting CPR are highlighted; Fig. 1B shows a sequence (SEQ ID NO: 4) of PCI showing the disulfide bond configuration (Cys8 Cys24, Cys12 Cys27 and Cys18 Cys 34); Fig. 1C shows a partial crystal structure of PCI, showing the spatial arrangement of the basic residues (Lys10, Lys13 and Arg32); and Fig. 1D shows sequences and molecular weight of the PCI-derived peptides (PCI-2K (SEQ ID NO: 1). PCI-R (SEQ ID NO: 2), and PCI-2K-R (SEQ ID NOS 1 and 2)), the novel inhibitory peptide (CPI-2KR) (SEQ ID NO: 3) and CPI-2KR-cyclic (SEQ ID NO: 3);

FIG. 2 shows competitive inhibition of PCI and PCI-2K-R against CPRA, wherein FIG. 2B shows kinetic constants (Vmax, Km, $K_{cat}$ and Ki) for CPR alone and in the presence of PCI and PCI-2K-R; and FIG. 2C shows CPR binding to PCI-derived 10-mer peptides (SEQ ID NOS 5–34 respectively in order of appearance) on a cellulose membrane;

FIG. 3 shows competitive inhibition of CPI-2KR against CPR.A, wherein FIG. 3C shows the lineweaver-Burke plot (1/v versus 1/[S]) for CPI-2KR at various concentrations (63, 126 and 253 nM) relative to no inhibitor (0 mM); FIG. 3D shows the dixon plot (1/v versus [I]) for CPI-2KR for increasing substrate concentrations (1.2 6.0 mM; indicated by arrow); and FIG. 3E shows kinetic constants (Vmax, Km, $k_{cat}$ and Ki) for CPR alone and in the presence of CPI-2KR;

FIG. 4 shows CD spectra of CPR, CPI-2KR and the CPR/CPI-2KR complex, wherein

FIG. 5 shows NMR and molecular modeling studies, wherein FIG. 5A shows $C_a$—$C_a$ distance ( ) between the basic residues of PCI-2K-R, CPI-2KR, CPI-2KR-cyclic and PCI; and FIG. 5B shows an energy minimized structure of CPI-2KR showing the $C_a$—$C_a$ distance ( ) between the basic residues; FIG.5C shows an energy minimized structure of CPI-2KR-cyclic showing the $C_a$—$C_a$ distance ( ) between the basic residues; and FIG. 5D sows an NMR structure of CPI-2KR-cyclic showing the $C_a$—$C_a$ distance ( ) between the basic residues;

FIG. 6 shows inhibition of CPN by GEMSA(not CPI-2KRA), wherein

DETAILED DESCRIPTION OF PREFERRED EMBODIMENT

Figure 2A:
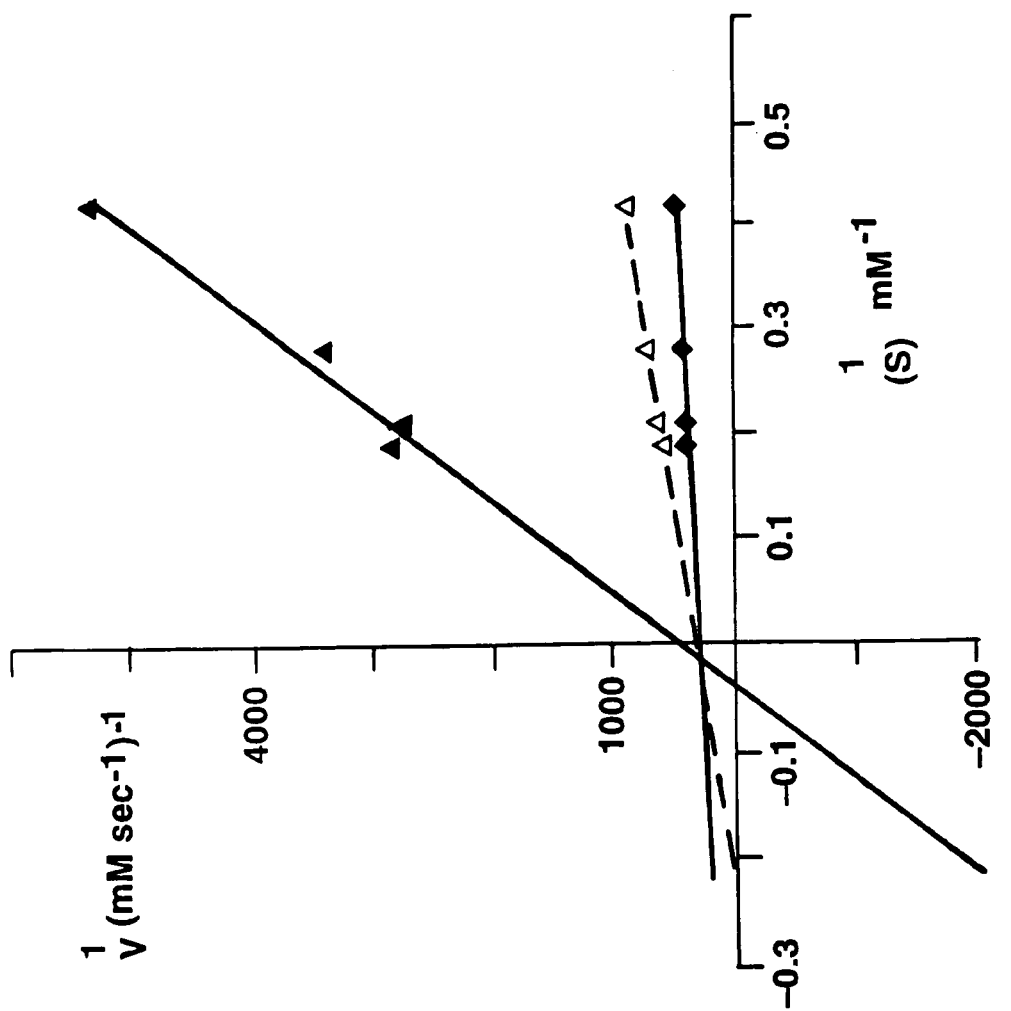
FIG. 2A shows the lineweaver-Burke plot (1/v versus 1/[s]) for PCI and PCI-2K-R showing competitive inhibition relative to no inhibitor.

To date no physiological inhibitor of CPR has been isolated, although metallocarboxypeptidase inhibitors have been found in potatoes [20], tomatoes [29], roundworms [30], leeches [31] and in some mammalian tissues [32]. Of these, potato carboxypeptidase inhibitor (PCI; Ki=0.4 nM) represents the most extensively studied one. Numerous non-specific CP inhibitors, some of which are highly toxic in vivo precluding their use for therapeutic application, also inhibit CPR-zinc chelators such as 1,10-phenantroline and EDTA, by ACA (Ki=0.8 mM), dithiothreitol, 2-mercaptoethanol, 2-mercaptomethyl-3-guanidino ethylthiopropanoic acid (MERGETPA), 4-chloromercuribenzoic acid, and the sulfur containing analogues of arginine and lysine, guanidinoethylmercaptosuccinic acid (GEMSA; Ki=18 mM) and amino propylmercaptosuccinic acid (APMSA), respectively [33]. Although GEMSA is the more potent inhibitor of the two basic amino acid analogues, it cannot differentiate between CPR and CPN precluding its use for therapeutic applications. Nonetheless, the physicochemical properties of this small organic molecule were incorporated into the design of our novel CPR inhibitor.

Due to its ability to inhibit CPR (not CPN), PCI has frequently been used to assess CPR activity both in vitro [22, 34] and in vivo [35]. Supplementing t-PA doses with PCI have been shown to enhance thrombolytic therapy in an animal model [19]. However, it should be noted that although PCI selectively inhibits CPR in the circulation, it also inhibits CPs found in the digestive tract (pancreatic CPB) and brain, pituitary, pancreatic islet and other neuro-endocrine cells (CPE/CPH) possibly causing other serious side effects upon administration [36]. Therefore, the development of a more specific CPR inhibitor of low molecular weight without toxicity is highly desirable.

PCI is a 39-residue protein belonging to the cystine knottin family [37]. Due to the presence of three disulfide bonds (FIG. 1A) it has a compact structure, comprising a globular core (Cys8-Cys34) and flexible N— and C-termini (Glu1–Ile7 and Glu35–Ly39, respectively). At present, no structural data is available for CPR due to its instability, however, the structure of PCI complexed with carboxypeptidase A (CPA) is available, which shows that PCI binds to CPA through its C-terminus [38, 39]. Although the specificity of CPA and CPR differs, the current assumption is that PCI also binds to CPR through its C-terminus. The inventors' studies, however, have shown that the tetrapeptide C-terminal fragment of PCI does not inhibit CPR (data not shown). In addition, other longer N- and C-terminal peptide fragments of PCI (FIG. 1B) also showed no inhibitory activity against CPR (data not shown), suggesting that the mechanism of inhibition is more complex.

Furthermore, studies have shown that the C-terminal Glu66 residue of leech carboxypeptidase inhibitor (LCI) is removed by both pancreatic CPA2 and CPB, which have a restricted specificity for aromatic and positively charged C-terminal residues, respectively, without affecting its inhibitory activity [31]. The C-terminus of LCI does not appear to be responsible for the inhibitory activity observed against these CPs. In addition, the removal of the C-terminal residue of PCI has also been reported and similarly may not affect the inhibitory activity of this CP inhibitor. In agreement with this observation, the results also suggest that the C-terminus of PCI may not be responsible for its inhibitory activity against CPR further suggesting that PCI interacts with CPR, and possibly other CPs, through other residues. Since the function of CPR is to remove C-terminal K and R residues from fibrin clots and inflammatory mediators, respectively, the inventors investigated the possibility that PCI inhibits CPR by competitively binding via these residues. Close inspection of the X-ray structure of PCI complexed to CPA revealed that the two K and single R residue(s) of the former are orientated in the same direction (FIG. 1A). Furthermore, these residues are in one plane (FIG. 1C), directly opposite the primary (residues 37–39) and secondary (residues 15, 23, 28, 29 and 30) binding domains of PCI for CPA (FIG. 1A). The possible involvement of these basic residues for the inhibition of CPR was subsequently examined.

The inventors designed and synthesized two peptide fragments, which mimicked the PCI regions possibly responsible for the observed inhibitory activity. The first peptide (PCI-2K) contained the two lysine residues and the second peptide (PCI-R) contained the arginine residue (FIG. 1D). These peptides represent two regions of PCI maintained in close spatial proximity by three disulfide bridges. As a starting point, under high dilution conditions, equimolar amounts of peptides PCI-2K and PCI-R, both containing a single cysteine residue, were oxidised to form the heterodimer PCI-2K-R. In contrast to the monomeric peptides, for which no activity was observed (data not shown), the heterodimer, PCI-2K-R, was found to be a weak competitive inhibitor of CPR (FIG. 2A). Furthermore, kinetics studies revealed that compared to PCI (Km 12.3 mM; Ki 1.4 nM; FIG. 2B), the inhibitory activity of PCI-2K-R was 290-fold lower (Km 4.2 mM; Ki 407.1 nM; FIG. 2B). The reduced inhibitory activity of this PCI-derived peptide may be attributed to the absence of two of the three disulfide bridges founds in wild type PCI, effectively resulting in increased mobility of all residues. To support these results, the interaction between CPR and 10-mer PCI peptide fragments synthesized on a cellulose membrane was also examined. The results, shown in FIG. 2C, indicated that CPR bound with peptides containing two K residues and also with peptides containing an R residue at their N-terminus. Inaccessible K and R residues, located proximal to the membrane did not interact appreciable with CPR.

Figure 3A:
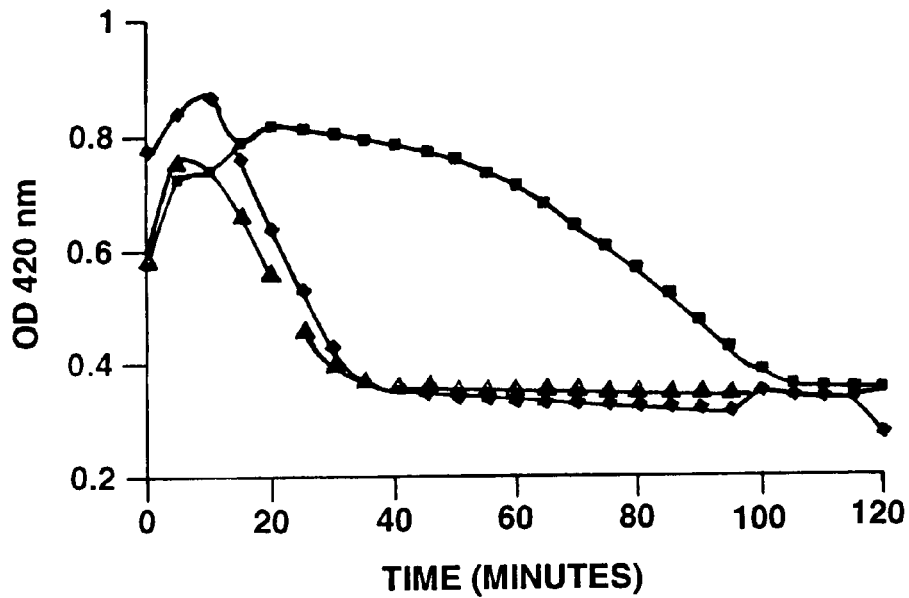
FIG. 3A shows in vitro TM-induced retardation of t-PA-induced fibrinolysis due to the conversion of proCPR to CPR by the T/TM complex.

In human plasma, t-PA-induced fibrinolysis is suppressed by the addition of TM (<10 nM). This suppression should be due to the conversion of proCPR to its active CPR form, which is inhibited by the presence of PCI (12 nM), thus permitting fibrinolysis to proceed (FIG. 3A). However, the heterodimeric peptide PCI-2K-R could not reverse the TM-induced retardation of t-PA-induced fibrinolysis (data not shown). The competitive inhibition of PCI-2K-R might not be strong enough to support t-PA function.

In view of the promising results obtained for the peptide PCI-2K-R, the crystal structure of PCI was more closely examined. In particular, the spatial C–$C_a$ distances between the K and R residues were measured (FIG. 1C). Subsequently, a novel linear peptide (CPI-2KR; FIG. 1D) was designed based on the data obtained from PCI. The peptide included the two K and single R residues from PCI (K10, K13 and R32) expected to be responsible for the interaction observed between PCI and CPR. The spatial separation of these basic residues was approximated to resemble that of PCI. In addition, the proline (P11) residue adjacent to K10 and the alanine (A31) adjacent to the R32 of PCI residue were included. At the N- and C-termini, cysteine (C) residues were added so as to permit cyclisation of the peptide and reduce conformational flexibility (CPI-2KR-cyclic; FIG. 1C). The C residue between the two K residues (K10 and K13; FIG. 1C) was replaced by an alanine residue to remove any possible interference with cyclisation. Finally, considering an asparagine (N29) residue is located in close spatial proximity to K13 and R32 in the crystal structure of PCI (see FIG. 1B), an asparagine residue was placed between the K5 and R8 of CPI-2KR. Asparagine is not a particularly reactive amino acid. However, it can act as both a hydrogen bond donor and acceptor under favorable conditions and its presence may therefore influence the activity of the peptide.

Figure 3B:
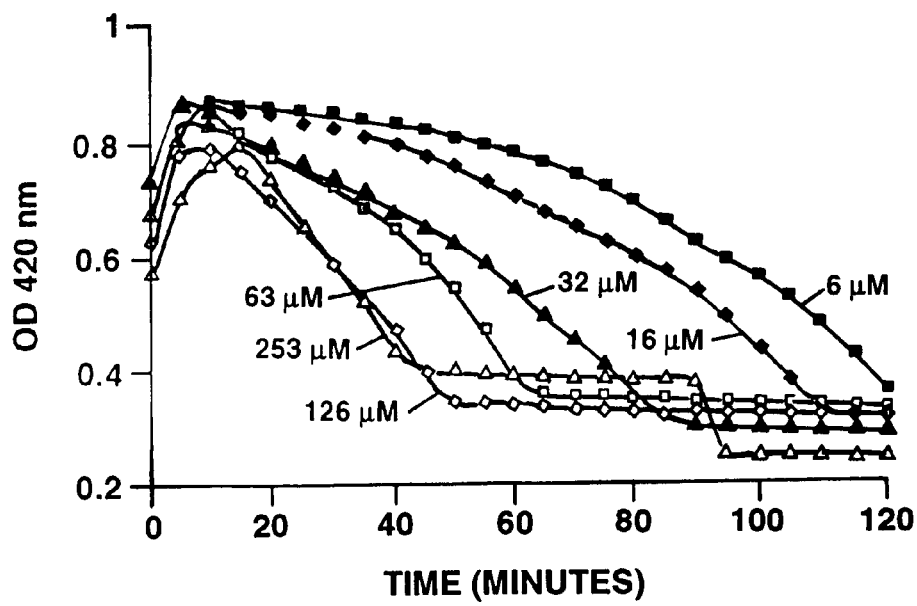
FIG. 3B shows dose-dependent inhibition by CPI-2KR at various concentrations (8, 16, 32, 63, 126 and 253 M) on the TM-induced retardation of t-PA-induced fibrinolysis.

Peptide CPI-2KR was assayed for its ability to reverse the TM-induced retardation of t-PA-induced fibrinolysis. Remarkably, this short linear peptide showed dose-responsive inhibition of TM-induced retardation of t-PA-induced fibrinolysis (FIG. 3B), although the effective inhibitory concentration of CPI-2KR (126 nM) was 10-fold higher that of PCI (12 nM). In contrast, cyclisation of the peptide (CPI-2KR-cyclic) resulted in a dramatic loss of inhibitory activity (data not shown), indicating that a certain degree of freedom is required for binding of this peptide to CPR. Furthermore, mutation studies indicated that the basic and C residues of CPI-2KR are essential for inhibitory activity. In particular, replacement of the basic residues by alanine residues or removal of the N- and C-terminal C residues or replacement of these residues by either alanine or methionine (M) resulted in a loss of biological activity (data not shown).

In order to gain insight into the inhibitory mechanism of CPI-2KR against CPR, a classical Henri-Michaelis-Menten kinetics analysis was performed. Since the Lineweaver-Burke plot (FIG. 3C) is prone to error, particularly at low concentrations of inhibitor and substrate, the Dixon plot (1/v versus [I]) was employed to evaluate the inhibitory mechanism of CPI-2KR (FIG. 3D). Replotting of the slopes of the Dixon plot against 1/[S] confirmed that CPR-2KR is a competitive inhibitor of CPR given that the line went through the origin (FIG. 3D insert). The Km $Km_{app}$ and Vmax were determined from the data obtained for no inhibitor and the highest inhibitor concentration (253 nM) from the Lineweaver-Burke plots (FIG. 3E). These values were in turn used to calculate the dissociation constant of CPI-2KR (Ki). CPI-2KR was found to have a relatively low Ki (8.8 nM; 6-fold higher than that of PCI), indicating that it binds to CPR with a relatively strong affinity. Of particular interest is the significant improvement in binding affinity for CPR (~46-fold stronger than PCI-2K-R), with the observed concomitant increase in inhibitory activity, when compared to PCI-2K-R. This may be attributed to the close spatial proximity of the K and R residues in the absence of disulfide bridges as for PCI.

Figures 4A, 4B:
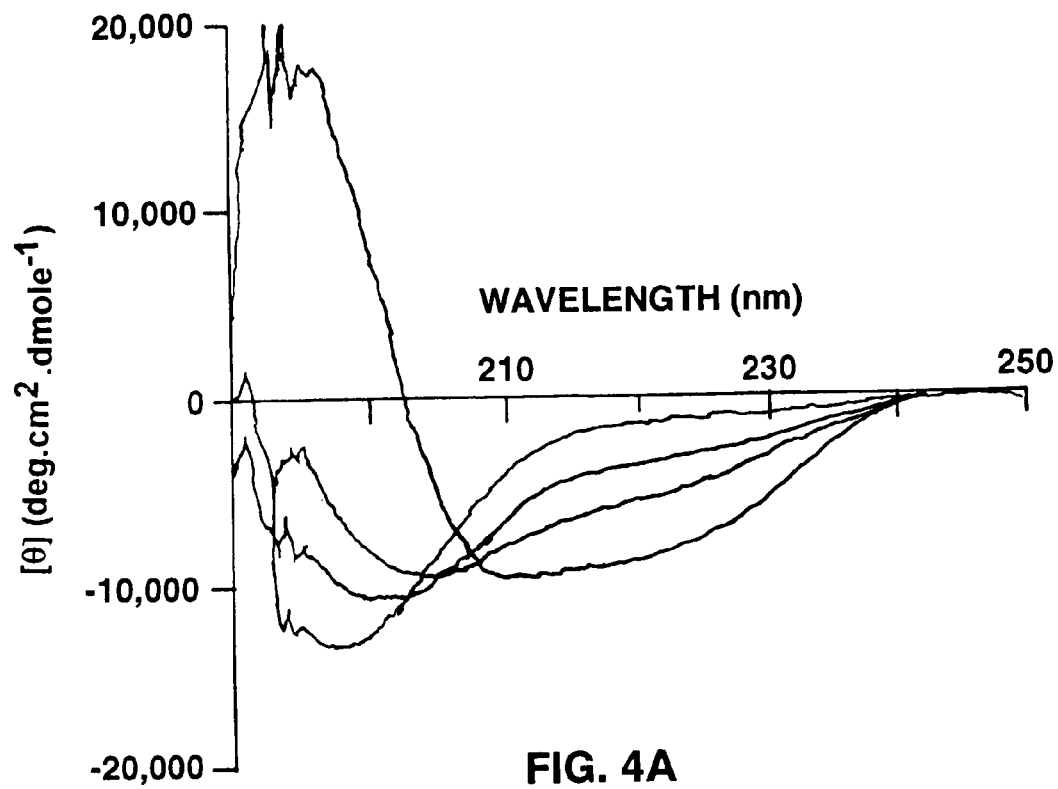
FIG. 4A shows CD spectra of CPR, CPI-2KR and the CPR/CPI-2KR complex immediately after mixing (Complex$_0$) and 30 minutes after mixing (Complex$_{30}$)
FIG. 4B shows a secondary structure estimations determined for the CD spectra shown in FIG. 4A.

Using similar conditions to those of the enzyme kinetics studies, circular dichroism (CD) spectroscopy was employed to analyze the solution conformation of CPR alone and when complexed with CPI-2KR. Due to the instability of CPR, the studies were performed at 4 C. After mixing CPI-2KR (150 mM) with CPR (1.1 mM), a significant change in the CD spectrum was observed which differed from the arithmetic sum of the individual spectra (FIG. 4A). The peptide is predominantly in a random conformation and CPR predominantly contains a-helical and b-sheet structure (FIG. 4B). Compared to the arithmetic sum, the CD spectra of the CPR/CPI-2KR complex immediately after mixing (Complex$_0$) shows significantly less random structure, particularly after 30 minutes incubation at 4° C. (Complex$_{30}$), suggesting that the conformation of CPR was altered when the CPR/CPI-2KR complex was formed.

Nuclear magnetic resonance (NMR) and molecular modeling (MM) studies provided insight into the possible conformation of the cyclic and linear peptides. Preliminary MM studies revealed that CPI-2KR can adopt a conformation with K and R residue $C_a$—$C_a$ distances comparable to those of PCI (FIG. 5A). The lowest energy conformation, following high temperature simulated annealing energy minimization, is shown in FIG. 5B. Although the Arg8-Lys2 $C_a$—$C_a$ distance is almost half that of PCI, this peptide is flexible enough, due to the lack of a disulfide bridge between the terminal Cys residues, to adopt a more suitable conformation to bind to CPR. For comparison, the cyclic peptide (CPI-2KR-cyclic) was also subjected to this procedure (FIG. 5C), however, due to steric hindrance the $C_a$—$C_a$ distances of K and R were significantly different to those of PCI (FIG. 5A). Although NMR spectroscopy could not provide any structural information for the linear peptide due to the large conformational flexibility of the molecule, the cyclic peptide structure was deduced (FIG. 5D). From this data we can see that the spatial separation of the K and R residues, for both the model and NMR structures of CPI-2KR-cyclic, significantly differ from those of PCI. Furthermore, the $C_a$—$C_a$ distances of K and R of the NMR structure of CPI-2KR-cyclic significantly differed from those of model structure obtained using the high temperature simulated annealing protocol. However, despite this our studies showed that a cyclic 9-mer peptide cannot have all basic residue side chains facing in the same direction. In both cases, one of the K residues is in the down position, while the other K and the R residues are in the up position. Therefore, CPI-2KR-cyclic might be unable to adopt a suitable conformation for binding to CPR due to steric hindrance.

Figures 6A, 6B:
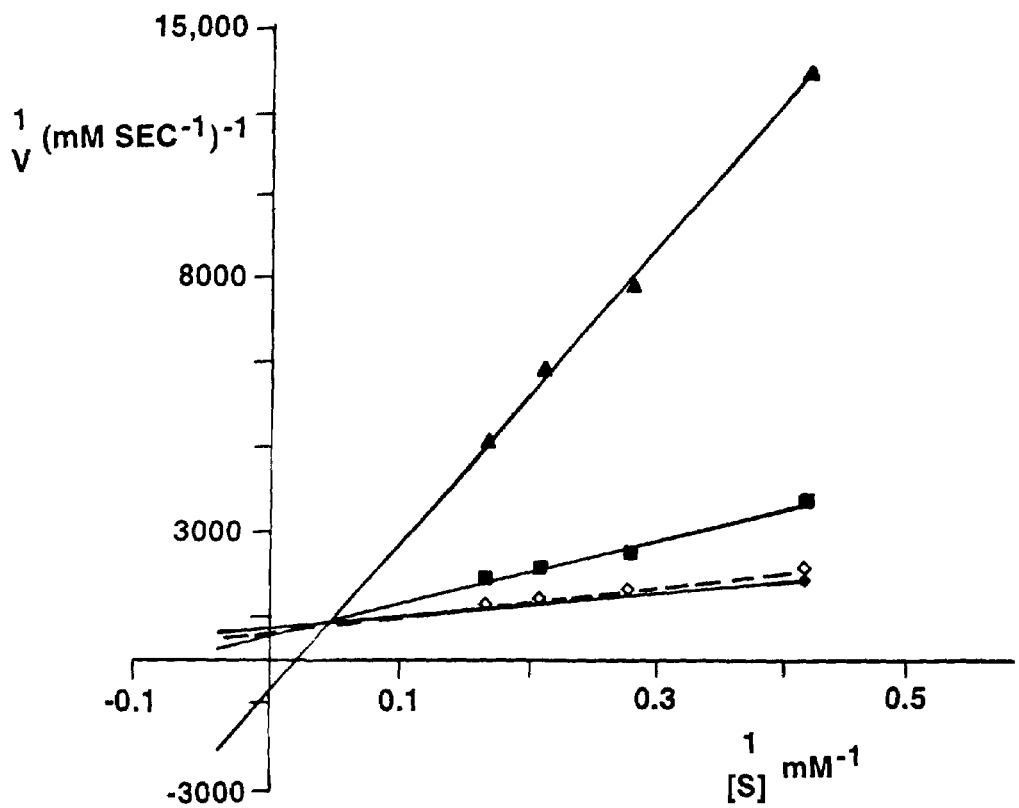
FIG. 6A shows the lineweaver-Burke plot (1/v versus 1/[S]) for GEMSA (closed square and closed triangle; 425 and 2126 nM, respectively) and CPI-2KR (506 nM) relative to no inhibitor.
FIG. 6B shows kinetic constants (Vmax Km and $k_{cat}$) for CPN alone and in the presence of GEMSA and CPI-2KR. The $R^2$ values for the linear regressions are included.

Finally, as shown in FIG. 6, CPI-2KR did not exhibit any inhibitory activity against CPN at 506 nM, 2-fold higher than the concentration required for CPR inhibition (FIG. 6). In contrast, GEMSA, which inhibits CPR at 18 mM [40], inhibited CPN at a low concentration of 425 nM and showed strong inhibitory activity against CPN at a 5-fold higher concentration of 2.1 mM.

CPI-2KR was designed using a rational structure-based strategy which combined information obtained from the crystal structure of a known CPR inhibitor, namely PCI, and the biological known function of the enzyme. Taken together, the information yielded a successful peptide candidate, which effectively lowered the TM-induced retardation of t-PA-induced fibrinolysis similar to PCI, acting through a competitive inhibitory mechanism, specifically inhibiting CPR without affecting CPN. This small novel CPR inhibitor is thus a useful agent for use in the prevention and/or treatment of thrombosis, while representing a lead molecule for the design of smaller organic molecules for use as adjuncts to thrombolytic therapy.

Peptides were synthesised using an AMS 422 Multiple Peptide Synthesiser (ABiMED, Langenfeld, Germany) using standard solid-phase synthesis techniques and 9-fluorenylmethoxycarbonyl (Fmoc) amino acids (Watanabe Chemical Industries Ltd., Hiroshima, Japan). In situ activation was by 2-(1H-Benzotriazole-1-yl) -1,1,3,3-tetramethyluronium hexafluorophosphate (HBTU) with N-methylmorpholine (NMM), and hydroxybenzotriazole (HOBT) as catalytic bases. Amidated peptides (25 mmole scale) were prepared using Fmoc-PAL-PEG-PS resin (PerSeptive Biosystems; Warrington, UK). All residues were double coupled in N,N-dimethylformamide (DMF; Peptide synthesizer grade; Watanabe Chem. Ind. Ltd.) N-methylpyrrolidone (NMP) and dichloromethane (DCM). Deprotection was achieved using 20% pipiredine in DMF.

Peptides were then cleaved from the resin, with concomitant removal of side-chain protecting groups by treatment with trifluoroacetic acid (TFA; 80%), thioanisol (12%), 1,2-ethanedithol (EDT; 6%), and m-cresol (2%). After cleavage, the peptides were precipitated with 2 volumes of cold ether for 10 min, collected by centrifugation, washed two times with cold ether and left to dry overnight. Purification was carried out by reversed-phase HPLC (Waters 741 Data Module, Waters 484 Tunable Absorbance Detector; Waters 600E System Controller). Samples of crude peptide were chromatographed on a Waters Delta-Pak™ $C_{18}$ column (40' 100 mm, 15 mm, 100 particles) with linear gradient: Milli-Q water/acetonitrile in 0.1% TFA. Peptide mass was confirmed using matrix-assisted laser desorption time-of-flight (MALDI-TOF) mass spectrometry (Kompact Maldi II, Kratos Analytical, Shimadzu, Japan). Lyophilized peptides were stored desiccated at –30° C.

The heterodimer, PCI-2K-R was formed by mixing equimolar amounts (ca. 1 mM in Milli-Q water/0.5% acetic acid) of PCI-2K and PCI-R in 500 ml of Milli-Q water (pH 8.2). After mixing for at least one day, the pH was readjusted to 2.2 and the solution was filtered through a 0.45 micron filter and desalted using isocratic conditions (50% acetonitrile) on a Waters Delta-Pak™ $C_{18}$ column. The heterodimeric peptide (CPI-2KR) was separated from the monomeric (PCI-2K and PCI-R) and homodimeric species using linear gradient conditions identical to those outlined in the Peptide Synthesis section (above).

The formation of disulfide bonds was indirectly determined by monitoring the absence of SH groups. Ellman's reagent (DTNB; 5,5'-Dithio-bis(2-nitrobenzoic acid); 0.1 mM; [41] in potassium dihydrogen phosphate (1.2 mM), disodium hydrogen phosphate buffer (95 mM) forms a mixed disulfide with thiols, liberating the chromophore 5-mercapto-2-nitrobenzoic acid (absorption maximum 410 nm, ~13, 600 cm$^{-1}$M$^{-1}$). Peptide solutions (0.25 mM) were mixed with increasing concentrations of Ellman's reagent (0, 0.03, 0.06 0.075 mM) and read at 412 nm.

Cellulose-bound overlapping peptides (10-mers) derived from PCI were prepared using an Auto-Spot Robot ASP 222 peptide synthesiser (ABiMED, Langenfeld, Germany; Software DIGEN, Jerini BioTools GmbH, Berlin, Germany) on Whatman 50 (Whatman, Maidstone, United Kingdom) membranes [42]. Anchor groups were obtained by homogeneous derivatisation of the hydroxyl groups with Fmoc-b-alanine. Following deprotection, using 20% pipiredine in DMF, Fmoc amino acids (0.5 M), activated using HOBT and N, N'-diisopropylcarbodiimide (DIPCI), were applied and allowed to react for 20 minutes. After 10 cycles, the side-chain protecting groups were removed using trifluoroacetic acid (TFA; 80%), thioanisol (12%), 1,2-ethanedithol (EDT; 6%), and m-cresol (2%).

Membranes were washed four times with phosphate buffered saline/0.05% Tween20 (pH 7.3; PBS-T) and blocked with PBS-T-1% BSA overnight at 4° C. CPR (10 mg/ml in blocking solution) or PBS-T-1% BSA (control) were allowed to interact with the bound peptides at 4° C. overnight. The following day, membranes were incubated with an FITC-conjugated anti-proCPR monoclonal antibody, 10G1 (10G1-FITC; 10 mg/ml) which also recognizes CPR [43], subsequent to being washed four times with PBS-T, twice with PBS-T-1M NaCl and twice with PBS-T. After 4 hours incubation at room temperature, the membranes were read on a fluorescence laser scanner (FLA3000; Fujifilm, Japan) and analyzed using the Array Gauge software (version 1.0; Fujifilm, Japan).

ProCPR was purified to homogeneity as previously described [3]. The pure enzyme showed a single band by SDS-polyacrylamide gel electrophoresis (SDS-PAGE) at 60 kDa and was converted by thrombin/thrombomodulin to the activated form resulting in a band at approximately 35 kDa in SDS-PAGE analysis. CPN was purified to homogeneity as previously described [8]. The enzyme gave three bands on SDS-PAGE at 83 kDa, 53 kDa and 50 kDa corresponding to the two large identical glycosylated subunits and the two smaller active subunits, respectively.

The activity of the CPR inhibitors was determined against purified CPR using hippuryl-L-arginine as the substrate. The peptides PCI-2K-R, CPI-2KR, PCI (500, 250/125/62.5, 50 mg/ml, respectively) or Tris-HCl buffer (50 mM; pH 7.5) were added to active CPR (40–320 mg/ml) at a 1:7 ratio. After thorough mixing, 20 ml was incubated with various concentrations of hippuryl-L-arginine (1.2–6.0 mM), for 15 minutes at 37° C. The reaction was stopped with the addition of sodium phosphate buffer (100 ml; 0.25 M), immediately followed by 3% cyanuric chloride in 1,4-dioxane (75 ml) [21]. After mixing well, the generation of hippuric acid was determined by measuring the OD at 405 nm on a Spectra-MAX 250 Microplate Spectrophotometer (Molecular Device Corporation, Sunnyvale, Calif., USA). Hippuric acid (0–2.0 mM) in Tris buffer was used as the standard.

A kinetics analysis of the CPR-catalysed hydrolysis of hippuryl-L-arginine in the absence and presence of inhibitory molecules was performed. The Lineweaver-Burk reciprocal plot, based on rearrangement of the Henri-Michaelis-Menten equation into a linear form, was applied:

$$\frac{1}{v} = \frac{K_m}{V_{max}} \frac{1}{[S]} + \frac{1}{V_{max}}$$

where v (in mM sec$^{-1}$) is the instantaneous or initial velocity, [S] (mM) is the substrate concentration, Km(mM)is equivalent to the substrate concentration that yields half-maximal velocity and Vmax(mM sec$^{-1}$) is the maximum velocity. For competitive inhibition, where the inhibitor competes with the substrate for binding to the enzyme, the following mechanism was assumed:
where

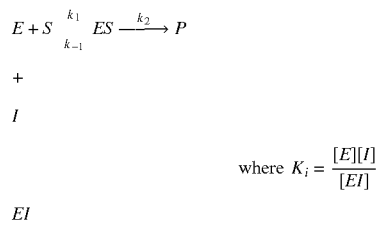

$$E + S \underset{k_{-1}}{\overset{k_1}{\rightleftharpoons}} ES \xrightarrow{k_2} P$$
$$+$$
$$I$$
$$\updownarrow$$
$$EI$$

where $K_i = \frac{[E][I]}{[EI]}$

In competitive inhibition, the apparent Vmax is not affected with increasing inhibitor concentrations because once substrate binds the reaction proceeds normally (i.e. Vmax depends only on maximum ES complex concentration, which only depends on the total amount of enzyme present) However, the apparent Km increases (i.e. a higher substrate concentration is required for a given velocity) by a factor of [1+([I]/Ki)]. Therefore, the dissociation constant for a competitive inhibitor, Ki, can be calculated from:

$$K_{m_{app}} = K_m \left(1 + \frac{[I]}{K_i}\right)$$

where Km$_{app}$ is the apparent Km for a given inhibitor concentration.

The Dixon plot (1/v versus [I] in the presence of different concentrations of substrate) provides a more diagnostic way of identifying the type of inhibition and determining the Ki:

$$\frac{1}{v} = \frac{K_m}{V_{max} K_i [S]} [I] + \frac{1}{V_{max}} \left(1 + \frac{K_m}{[S]}\right)$$

Since a linear mixed-type inhibitor yields the same type of Dixon plot as a competitive inhibitor, the slopes of the Dixon plots versus 1/[S] can be replotted to distinguish one from the other. For a competitive inhibitor, the slope replot goes through the origin while that for a mixed-type inhibitor does not.

The effect of CPI-2KR on purified CPN was determined using hippuryl-L-arginine as the substrate. Guanidinoethylmercaptosuccinic acid (GEMSA) was used as a positive control. CPI-2KR (500 mg/ml), GEMSA (100, 500 mg/ml) or Tris-HCl buffer (50 mM; pH 7.5) were added to CPN (10 mg/ml) at a 1:7 ratio. Identical conditions to those used for the CPR kinetics experiments were subsequently applied.

Human plasma was obtained by centrifugation of citrated blood at 3000 g for 15 minutes at room temperature. In a 96-well microtitre plate, 20 ml of a thrombin/calcium mix [50 ml calcium (CaCl Q; 1 M), 20 ml of thrombin (T; 500 U/ml) and 430 ml of Tris buffer (50 mM, pH 7.5)] was added followed by 10 ml of thrombomodulin (TM; final concentration 8 nM). Subsequently, 10 ml of peptide solution in Tris buffer (16 mg/ml 500 mg/ml), Tris buffer or PCI (50 mg/ml) were added. After the addition of 50 ml of a t-PA/plasma mix [8 ml of t-PA (130 mg/ml) mixed with 1 ml of pre-warmed citrated plasma (37° C. for 5 minutes) ] the plate was immediately read at 420 nm every 5 minutes for 2 hours on a SpectraMAX 250 Microplate Spectrophotometer (Molecular Device Corporation, Sunnyvale, Calif., USA). Lysis time was defined as the time required for the absorbance to reach half the difference between the plateau reached after clotting and baseline achieved at clot lysis.

Samples were prepared by dissolving CPI-2KR or CPI-2KR-cyclic in 500 ml of water containing 10% D$_2$O. The final peptide concentration of the solution was 3 mM. The pH of the sample solution was adjusted to 5.0. NMR experiments were carried out at 5° C. on a Bruker DMX-500 spectrometer. Two-dimentional NMR experiments including HOHAHA [44] and ROESY [45] were carried out using the WATERGATE scheme for water suppression [46], while in the case of DQF-COSY [47], a low-power irradiation of the water frequency was used during the relaxation delay. HOHAHA spectra were recorded with mixing time of 60 ms. ROESY spectra were recorded with mixing times of 200 ms, 300 ms, and 400 ms. Processing and analyses of the spectra were done using the Bruker XWINNMR.

Inter-proton distance constraints were obtained from the ROESY spectra observed with mixing times of 300 ms. Observed ROE data were classified into four distance ranges, 1.8–2.7, 1.8–3.5, 1.8–5.0 and 3.0–6.0, corresponding to strong, medium, weak and very weak ROE values, respectively. The upper boundary of NOEs involving amide protons was extended to 2.9 for strong ROEs and to 3.5 for medium ROEs to account for the higher observed intensity of this type of intensity [48]. In addition, a 0.5 correction [48] was added to the upper boundary of the distances involving methyl protons. Structure calculations were performed on 41 inter-proton distance constraints derived from the 2D ROESY spectrum, 7 dihedral angle constraints derived from $^1$H 1D-NMR spectrum, and one disulfide bond restraint. All calculations were carried out using dynamic simulated annealing protocols in the program DYNAMO. The structure was analyzed using the program PROCHECK [49].

A conformational search for the global energy minimum of the molecules (PCI-2K-R, CPI-2KR and CPI-2KR-cyclic) was performed using a molecular dynamics (MD) simulated annealing strategy. Initially, to relax the peptides from strain, a steepest descent minimization was applied for 5000 iterations, until a maximum derivative of less than 1.00 kcal/ was achieved. This was followed by conjugate gradient minimization for 10000 iterations, until a maximum derivative of 0.01 kcal/ was achieved. The system was subsequently equilibrated at 200 K for 10 ps and then rapidly heated to 900 K by increasing the temperature by 100 K every 1 ps. The configuration space was sampled at 900 K for 10 ps. After the high temperature dynamics, the system was cooled slowly by decreasing the temperature by 25 K every 1 ps, until the temperature reached 200 K. At this stage the system was re-equilibrated for a further 10 ps and the configuration space was sampled once again for 30 ps. The lowest energy conformation of each peptide from the MD simulation was selected for analysis. The $C_a$—$C_a$ distances between the basic residues of each peptide were measured using Insight II (MSI, SanDiego).

Circular dichroism spectra were measured over the range 190–250 nm, using a Jasco-715 spectropolarimeter (Jasco, Tokyo, Japan) coupled to an Eyela Cooling Thermo Pump CTP-200 (Tokyo Rikakikai Co. Ltd, Tokyo, Japan). Spectra were obtained in Tris-HCl (50 mM, pH 7.5) at 4° C. using a cell with a path length of 0.1 cm. CPR (40 mg/ml) and CPI-2KR (160 mg/ml) concentrations were similar to those used for the kinetics studies. Data points were recorded at a scan speed of 50 nm/min, bandwidth of 1.0 nm, 8 s response and 0.1 nm resolution. Four repeat scans were used to obtain the final averaged spectra. Following baseline correction, the observed ellipticity, was converted to mean residue ellipticity [] (deg.cm$^2$.dmole$^{-1}$), using the relationship:

$$[\theta] = \frac{\theta}{10 \cdot lcN}$$

where 1 is the path length in centimeters, c is the molar concentration and N is the number of residues in the protein/peptide. The percentage of a-helix, b-sheet, b-turn and random structure was estimated using the least squares method [50] and reference CD spectra [51] using the Protein Secondary Structure Estimation software V1.10.00 (Jasco, Tokyo, Japan).

References

1. Vendrell, J., Querol, E., and Aviles, F. X. (2000). Metallocarboxypeptidases and their protein inhibitors. Structure, function and biomedical properties. Biochim. Biophys. Acta 1477, 284–298.

2. Campbell, W. and Okada, H. (1989). An arginine specific carboxypeptidase generated in blood during coagulation or inflammation which is unrelated to carboxypeptidase N or its subunits. Biochem. Biophys. Res. Commun. 162, 933–939.

3. Eaton, D. L., Malloy, B. E., Tsai, S. P., Henzel, W., and Drayna, D. (1991). Isolation, molecular cloning, and partial characterization of a novel carboxypeptidase B from human plasma. J. Biol. Chem. 266, 21833–21838.

4. Hendriks, D., Scharpe, S., van Sande, M., and Lommaert, M. P. (1989). Characterisation of a carboxypeptidase in human serum distinct from carboxypeptidase N. J. Clin. Chem. Clin. Biochem. 27, 277–285.

5. Bajzar, L., Manuel, R., and Nesheim, M. E. (1995). Purification and characterization of TAFI, a thrombin-activable fibrinolysis inhibitor. J. Biol. Chem. 270, 14477–14484.

6. Reynolds, D. S., Gurley, D. S., Stevens, R. L., Sugarbaker, D. J., Austen, K. F., and Serafin, W. E. (1989). Cloning of cDNAs that encode human mast cell carboxypeptidase A, and comparison of the protein with mouse mast cell carboxypeptidase A and rat pancreatic carboxypeptidases. Proc. Natl. Acad. Sci. U.S.A 86, 9480–9484.

7. Campbell, W., Okada, N., and Okada, H. (2001). Carboxypeptidase R is an inactivator of complement-derived inflammatory peptides and an inhibitor of fibrinolysis. Immunol. Rev. 180, 162–167.

8. Plummer, T. H., Jr. and Hurwitz, M. Y. (1978). Human plasma carboxypeptidase N. Isolation and characterization. J. Biol. Chem. 253, 3907–3912.

9. Plummer, T. H., Jr. and Ryan, T. J. (1981). A potent mercapto bi-product analogue inhibitor for human carboxypeptidase N. Biochem. Biophys. Res. Commun. 98, 448–454.

10. Skidgel, R. A., Deddish, P. A., and Davis, R. M. (1988). Isolation and characterization of a basic carboxypeptidase from human seminal plasma. Arch. Biochem. Biophys. 267, 660–667.

11. Tan, F., Jackman, H., Skidgel, R. A., Zsigmond, E. K., and Erdos, E. G. (1989). Protamine inhibits plasma carboxypeptidase N, the inactivator of anaphylatoxins and kinins. Anesthesiology 70, 267–275.

12. Shinohara, T., Sakurada, C., Suzuki, T., Takeuchi, O., Campbell, W., Ikeda, S., Okada, N., and Okada, H. (1994). Pro-carboxypeptidase R cleaves bradykinin following activation. Int. Arch. Allergy Immunol. 103,400–404.

13. Wang, W., Boffa, M. B., Bajzar, L., Walker, J. B., and Nesheim, M. E. (1998). A study of the mechanism of inhibition of fibrinolysis by activated thrombin-activable fibrinolysis inhibitor. J. Biol. Chem. 273, 27176–27181.

14. Redlitz, A., Tan, A. K., Eaton, D. L., and Plow, E. F. (1995). Plasma carboxypeptidases as regulators of the plasminogen system. J. Clin. Invest 96, 2534–2538.

15. Christensen, U. (1985). C-terminal lysine residues of fibrinogen fragments essential for binding to plasminogen. FEBS Lett. 182, 43–46.

16. Fleury, V. and Angles-Cano, E. (1991). Characterization of the binding of plasminogen to fibrin surfaces: the role of carboxy-terminal lysines. Biochemistry 30, 7630–7638.

17. Vali, Z. and Patthy, L. (1984). The fibrin-binding site of human plasminogen. Arginines 32 and 34 are essential for fibrin affinity of the kringle 1 domain. J. Biol. Chem. 259, 13690–13694.

18. Nicole, O., Docagne, F., Ali, C., Margaill, I., Carmeliet, P., MacKenzie, E. T., Vivien, D., and Buisson, A.

(2001). The proteolytic activity of tissue-plasminogen activator enhances NMDA receptor-mediated signaling. Nat. Med. 7, 59–64.

19. Nagashima, M., Werner, M., Wang, M., Zhao, L., Light, D. R., Pagila, R., Morser, J., and Verhallen, P. (2000). An inhibitor of activated thrombin-activatable fibrinolysis inhibitor potentiates tissue-type plasminogen activator-induced thrombolysis in a rabbit jugular vein thrombolysis model. Thromb. Res. 98, 333–342.

20. Ryan, C. A., Hass, G. M., and Kuhn, R. W. (1974). Purification and properties of a carboxypeptidase inhibitor from potatoes. J. Biol. Chem. 249, 5495–5499.

21. Mosnier, L. O., dem Borne, P. A., Meijers, J. C., and Bouma, B. N. (1998). Plasma TAFI levels influence the clot lysis time in healthy individuals in the presence of an intact intrinsic pathway of coagulation. Thromb. Haemost. 80, 829–835.

22. Bajzar, L., Morser, J., and Nesheim, M. (1996). TAFI, or plasma procarboxypeptidase B, couples the coagulation and fibrinolytic cascades through the thrombin-thrombomodulin complex. J. Biol. Chem. 271, 16603–16608.

23. Boffa, M. B., Wang, W., Bajzar, L., and Nesheim, M. E. (1998). Plasma and recombinant thrombin-activatable fibrinolysis inhibitor (TAFI) and activated TAFI compared with respect to glycosylation, thrombin/thrombomodulin-dependent activation, thermal stability, and enzymatic properties. J. Biol. Chem. 273, 2127–2135.

24. Esmon, C. T. (2000). The endothelial cell protein C receptor. Thromb. Haemost. 83, 639–643.

25. Mosnier, L. O., Meijers, J. C., and Bouma, B. N. (2001). Regulation of fibrinolysis in plasma by TAFI and protein C is dependent on the concentration of thrombomodulin. Thromb. Haemost. 85, 5–11.

26. Kato, T., Akatsu, H., Sato, T., Matsuo, S., Yamamoto, T., Campbell, W., Hotta, N., Okada, N., and Okada, H. (2000). Molecular cloning and partial characterization of rat procarboxypeptidase R and carboxypeptidase N. Microbiol. Immunol. 44, 719–728.

27. Sato, T., Miwa, T., Akatsu, H., Matsukawa, N., Obata, K., Okada, N., Campbell, W., and Okada, H. (2000). Procarboxypeptidase R is an acute phase protein in the mouse, whereas carboxypeptidase N is not. J. Immunol. 165, 1053–1058.

28. van Tilburg, N. H., Rosendaal, F. R., and Bertina, R. M. (2000). Thrombin activatable fibrinolysis inhibitor and the risk for deep vein thrombosis. Blood 95, 2855–2859.

29. Martineau, B., McBride, K. E., and Houck, C. M. (1991). Regulation of metallocarboxypeptidase inhibitor gene expression in tomato. Mol. Gen. Genet. 228, 281–286.

30. Homandberg, G. A., Litwiller, R. D., and Peanasky, R. J. (1989). Carboxypeptidase inhibitors from Ascaris suum: the primary structure. Arch. Biochem. Biophys. 270, 153–161.

31. Reverter, D., Vendrell, J., Canals, F., Horstmann, J., Aviles, F. X., Fritz, H., and Sommerhoff, C. P. (1998). A carboxypeptidase inhibitor from the medical leech Hirudo medicinalis. Isolation, sequence analysis, cDNA cloning, recombinant expression, and characterization. J. Biol. Chem. 273, 32927–32933.

32. Normant, E., Martres, M. P., Schwartz, J. C., and Gros, C. (1995). Purification, cDNA cloning, functional expression, and characterization of a 26-kDa endogenous mammalian carboxypeptidase inhibitor. Proc. Natl. Acad. Sci. U.S.A 92, 12225–12229.

33. McKay, T. J. and Plummer, T. H., Jr. (1978). By-product analogues for bovine carboxypeptidase B. Biochemistry 17, 401–405.

34. Schatteman, K. A., Goossens, F. J., Scharpe, S. S., Neels, H. M., and Hendriks, D. F. (1999). Assay of procarboxypeptidase U, a novel determinant of the fibrinolytic cascade, in human plasma. Clin. Chem. 45, 807–813.

35. Klement, P., Liao, P., and Bajzar, L. (1999). A novel approach to arterial thrombolysis. Blood 94, 2735–2743.

36. Bouma, B. N., Marx, P. F., Mosnier, L. O., and Meijers, J. C. (2001). Thrombin-activatable fibrinolysis inhibitor (tafi, plasma procarboxypeptidase b, procarboxypeptidase r, procarboxypeptidase u). Thromb. Res. 101, 329–354.

37. Craik, D. J., Daly, N. L., and Waine, C. (2001). The cystine knot motif in toxins and implications for drug design. Toxicon39, 43–60.

38. Rees, D. C. and Lipscomb, W. N. (1980). Structure of the potato inhibitor complex of carboxypeptidase A at 2.5-A resolution. Proc. Natl. Acad. Sci. U.S.A 77, 4633–4637.

39. Rees, D. C. and Lipscomb, W. N. (1980). Structure of potato inhibitor complex of carboxypeptidase A at 5.5-A resolution. Proc. Natl. Acad. Sci. U.S.A 77, 277–280.

40. Hendriks, D., Wang, W., Scharpe, S., Lommaert, M. P., and van Sande, M. (1990). Purification and characterization of a new arginine carboxypeptidase in human serum. Biochim. Biophys. Acta 1034, 86–92.

41. Ellman GL. (1959). Tissue sulfhydryl groups. Arch. Biochem. Biophys. 82, 70–77.

42. Frank R. (1992). SPOT synthesis: an easy technique for the positionally addressable, parallel chemical synthesis on a membrane support. Tetrahedron 48, 9217–9232.

43. Guo, X., Morioka, A., Kaneko, Y., Okada, N., Obata, K., Nomura, T., Campbell, W., and Okada, H. (1999). Arginine carboxypeptidase (CPR) in human plasma determined with sandwich ELISA. Microbiol. Immunol. 43, 691–698.

44. Bax, A. and Davis, D. G. (1985). MLEV-17-based two-dimentional homonuclear magnetization transfer spectroscopy. J. Magn. Reson. 65, 355–360.

45. Bothner-By, A. A., Stephens, R. L., Lee, J. M., Warren, C. D., and Jeanloz, R. W. (1984). Structure determination of a tetrasaccharide: Transient nuclear Overhauser effects in the rotating frame. J. Am. Chem. Soc. 106, 811–813.

46. Piotto, M., Saudek, V., and Sklenar, V. (1992). Gradient-tailored excitation for single quantum spectroscopy of aqueous solutions. J. Biomol. NMR 2, 665.

47. Rance, M., Sorencen, O. W., Bodenhausen, G., Wagner, G., Ernst, R. R., and W thrich, K. (1993). Improved spectral resolution in COSY$^P$H NMR spectra of proteins via double quantum filtering. Biochem. Biophys. Res. Commun. 117, 479–485.

48. Qin, J., Clore, G. M., ennedy, W. P., uszeuski, J., and ronenborn, A. M. (1996). The solution structure of human thioredoxin complexed with its target from Ref-1 reveals peptide chain reversal. Structure 4, 620.

49. Laskowski, R. A., MacArthur, M. W., Moss, D. S., and Thornton, J. M. (1993). PROCHECK: a program to check the stereochemical quality of protein structures. J. Appl. Cryst. 26, 283–291.

50. Provencher, S. W. and Gl ckner, J. (1981). Estimation of Globular Protein Secondary Structure From Circular Dichroism. Biochemistry 20, 33–37.51.

51. Yang, J. T., Wu, C.-S., and Martinez, H. M. (1986). Calculation of Protein Conformation From Circular Dichroism. Methods Enzymol. 130,208–269.

* Document attached: Sequence Listing

What is claimed is:

1. A carboxypeptidase R inhibiting peptide having an amino acid sequence Cys-Lys-Pro-Ala-Lys-Asn-Ala-Arg-Cys (SEQ ID NO. 3).

2. A pharmaceutical preparation comprising the carboxypeptidase R inhibiting peptide of claim 1.

3. A carboxypeptidase R inhibiting peptide having an amino acid sequence Cys-Lys-Pro-Ala-Lys-Asn-Ala-Arg-Cys (SEO ID NO: 3), wherein a disulfide bridge is formed between the two cysteine residues.

4. A pharmaceutical preparation comprising the carboxypeptidase R inhibiting peptide of claim 3.

* * * * *

UNITED STATES PATENT AND TRADEMARK OFFICE
CERTIFICATE OF CORRECTION

PATENT NO. : 7,144,864 B2  Page 1 of 1
APPLICATION NO. : 10/254610
DATED : December 5, 2006
INVENTOR(S) : Hidechika Okada It is certified that error appears in the above-identified patent and that said Letters Patent is hereby corrected as shown below:

On the title page, in the list of Inventors (75), in the residence data for inventor William Campbell:

"Yoyohashi (JP)" should read -- Toyohashi (JP) --

Signed and Sealed this

Thirteenth Day of February, 2007

JON W. DUDAS
*Director of the United States Patent and Trademark Office*

SEQUENCE LISTING

<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Lys Pro Cys Lys Thr His Asp Asp
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ala Cys Trp Asn Ser Ala Arg Thr
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Lys Pro Ala Lys Asn Ala Arg Cys
 1               5

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln His Ala Asp Pro Ile Cys Asn Lys Pro Cys Lys Thr His Asp
 1               5                  10                  15

Asp Cys Ser Gly Ala Trp Phe Cys Gln Ala Cys Trp Asn Ser Ala Arg
            20                  25                  30

Thr Cys Gly Pro Tyr Val Gly
            35

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln His Ala Asp Pro Ile Cys Asn Lys
 1               5                  10

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Ala Asp Pro Ile Cys Asn Lys Pro
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ala Asp Pro Ile Cys Asn Lys Pro Cys
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Asp Pro Ile Cys Asn Lys Pro Cys Lys
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Pro Ile Cys Asn Lys Pro Cys Lys Thr
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Ile Cys Asn Lys Pro Cys Lys Thr His
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Ile Cys Asn Lys Pro Cys Lys Thr His Asp
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asn Lys Pro Cys Lys Thr His Asp Asp
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Lys Pro Cys Lys Thr His Asp Asp Cys
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Pro Cys Lys Thr His Asp Asp Cys Ser
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Cys Lys Thr His Asp Asp Cys Ser Gly
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Lys Thr His Asp Asp Cys Ser Gly Ala
 1               5                  10

<210> SEQ ID NO 17
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Thr His Asp Asp Cys Ser Gly Ala Trp
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr His Asp Asp Cys Ser Gly Ala Trp Phe
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Asp Asp Cys Ser Gly Ala Trp Phe Cys
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Asp Cys Ser Gly Ala Trp Phe Cys Gln
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Cys Ser Gly Ala Trp Phe Cys Gln Ala
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Ser Gly Ala Trp Phe Cys Gln Ala Cys
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Ala Trp Phe Cys Gln Ala Cys Trp
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ala Trp Phe Cys Gln Ala Cys Trp Asn
 1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Trp Phe Cys Gln Ala Cys Trp Asn Ser
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Phe Cys Gln Ala Cys Trp Asn Ser Ala
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Cys Gln Ala Cys Trp Asn Ser Ala Arg
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic

```
                peptide

<400> SEQUENCE: 28

Cys Gln Ala Cys Trp Asn Ser Ala Arg Thr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ala Cys Trp Asn Ser Ala Arg Thr Cys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Cys Trp Asn Ser Ala Arg Thr Cys Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Trp Asn Ser Ala Arg Thr Cys Gly Pro
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Asn Ser Ala Arg Thr Cys Gly Pro Tyr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Ser Ala Arg Thr Cys Gly Pro Tyr Val
1               5                   10

<210> SEQ ID NO 34
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ala Arg Thr Cys Gly Pro Tyr Val Gly
 1               5                   10
```